United States Patent
Ofoche et al.

(10) Patent No.: US 12,399,097 B2
(45) Date of Patent: Aug. 26, 2025

(54) APPLICATION OF MARSH FUNNEL THROUGH USE OF TRAINED ALGORITHM

(71) Applicant: The Texas A&M University System, College Station, TX (US)

(72) Inventors: Paul Ofoche, Bryan, TX (US); Samuel F. Noynaert, College Station, TX (US)

(73) Assignee: The Texas A&M University System, College Station, TX (US)

( * ) Notice: Subject to any disclaimer, the term of this patent is extended or adjusted under 35 U.S.C. 154(b) by 1184 days.

(21) Appl. No.: 17/014,579

(22) Filed: Sep. 8, 2020

(65) Prior Publication Data

US 2021/0072131 A1    Mar. 11, 2021

Related U.S. Application Data

(60) Provisional application No. 62/897,714, filed on Sep. 9, 2019.

(51) Int. Cl.
| | |
|---|---|
| *G01N 11/06* | (2006.01) |
| *E21B 21/06* | (2006.01) |
| *G01N 9/00* | (2006.01) |
| *G01N 9/36* | (2006.01) |
| *G01N 33/28* | (2006.01) |
| *G06N 20/20* | (2019.01) |

(52) U.S. Cl.
CPC .......... *G01N 11/06* (2013.01); *E21B 21/062* (2013.01); *G01N 9/00* (2013.01); *G01N 9/36* (2013.01); *G01N 33/2823* (2013.01); *G06N 20/20* (2019.01)

(58) Field of Classification Search
CPC . G01N 11/06; G01N 9/00; G01N 9/36; G01N 33/2823; G06N 20/20; E21B 21/062
USPC ........................................................... 703/9
See application file for complete search history.

(56) References Cited

U.S. PATENT DOCUMENTS

| | | | | | |
|---|---|---|---|---|---|
| 3,064,468 | A | * | 11/1962 | Muench ............. | G01N 11/02 73/54.13 |
| 4,662,030 | A | * | 5/1987 | Cooper ............. | G01N 11/06 73/224 |
| 6,474,143 | B1 | * | 11/2002 | Herod .............. | G01N 11/06 73/32 R |
| 7,461,542 | B2 | * | 12/2008 | Weisinger ......... | G01N 11/06 141/334 |

(Continued)

OTHER PUBLICATIONS (Real Time Determination of Rheological Properties of Spud Drilling Fluids Using a Hybrid Artificial Intelligence Technique, SPE, 2018, pp. 1-13 ) (Year: 2018).*

(Continued)

*Primary Examiner* — Iftekhar A Khan
(74) *Attorney, Agent, or Firm* — Jackson Walker LLP

(57) ABSTRACT

A method includes obtaining a density of a fluid and obtaining a Marsh funnel time associated with the fluid. The density of the fluid and the Marsh funnel time is provided to a processor. The processor derives properties of the fluid from the fluid density and the Marsh funnel time. A machine-learning algorithm is applied to the properties of the fluid. The machine-learning algorithm determines a plastic viscosity and a yield point of the fluid. Output of the machine-learning algorithm is stored for future use. Properties of the drilling fluid are adjusted based on the output of the machine learning algorithm.

18 Claims, 16 Drawing Sheets

(56) References Cited

U.S. PATENT DOCUMENTS

| | | | |
|---|---|---|---|
| 8,024,962 B2* | 9/2011 | Tonmukayakul | G01N 11/14 73/61.68 |
| 9,891,152 B2* | 2/2018 | Guo | G01N 11/06 |
| 10,989,046 B2* | 4/2021 | Al-Rubaii | E21B 21/08 |
| 2004/0069069 A1* | 4/2004 | Gysling | G01F 1/668 73/736 |
| 2004/0141183 A1* | 7/2004 | Larson | G01N 11/06 356/477 |
| 2008/0173075 A1* | 7/2008 | Dale | G01N 11/14 702/12 |
| 2008/0283294 A1* | 11/2008 | Colquhoun | G01N 9/002 175/48 |
| 2012/0203463 A1* | 8/2012 | Guo | G01N 11/06 702/50 |
| 2014/0260560 A1* | 9/2014 | Zamora | G01N 11/14 73/54.28 |
| 2014/0262516 A1* | 9/2014 | Larson | G01N 11/08 175/48 |
| 2018/0067033 A1* | 3/2018 | Kulkarni | G01N 11/00 |
| 2018/0259437 A1* | 9/2018 | Abhishek | G01N 33/4905 |
| 2019/0277130 A1* | 9/2019 | Zarate Losoya | E21B 49/003 |
| 2019/0323935 A1* | 10/2019 | Elkatatny | G01N 1/38 |
| 2020/0033174 A1* | 1/2020 | Nogueira | G01N 27/10 |
| 2020/0371084 A1* | 11/2020 | Havenga | G01N 33/2823 |
| 2021/0072131 A1* | 3/2021 | Ofoche | G01N 9/00 |
| 2021/0238938 A1* | 8/2021 | Jamison | E21B 21/08 |
| 2022/0107257 A1* | 4/2022 | Ofoche | G01N 11/08 |
| 2022/0107301 A1* | 4/2022 | Ofoche | G01N 11/14 |
| 2022/0291108 A1* | 9/2022 | Ofoche | E21B 41/00 |

OTHER PUBLICATIONS

Al-Azani et al. (Real Time Prediction of the Rheological Properties of Oil-Based Drilling Fluids Using Artificial Neural Networks, SPE, 2018, pp. 1-17) (Year: 2018).*

Elkatatny, et al. (Real Time Prediction of the Rheological Parameters of NaCl Water-Based Drilling Fluid Using Artificial Neural Networks, SPE, 2017, pp. 1-15) (Year: 2017).*

* cited by examiner

APPLICATION OF MARSH FUNNEL THROUGH USE OF TRAINED ALGORITHM

CROSS-REFERENCE TO RELATED APPLICATIONS

This application claims priority to, and incorporates by reference the entire disclosure of, U.S. Provisional Patent Application No. 62/897,714, filed on Sep. 9, 2019.

TECHNICAL FIELD

The present disclosure relates generally to fluid measurements and more particularly, but not by way of limitation, to systems and methods for determining fluid properties utilizing a Marsh funnel time.

BACKGROUND

This section provides background information to facilitate a better understanding of the various aspects of the disclosure. It should be understood that the statements in this section of this document are to be read in this light, and not as admissions of prior art.

The drilling fluid plays an important role in the rotary drilling of wells. Serving as the means through which drill cuttings are lifted and downhole pressures controlled, the measurement and monitoring of the mud properties will help improve the safety of operations. The density determines the hydrostatic pressure while the rheology (viscosity) affects the lifting capacity. A well-established method of measuring fluid rheology continuously has yet to be adopted by the petroleum industry. The present disclosure reveals the use of an acoustical technique to obtain real-time measurements of fluid rheological properties and density.

SUMMARY OF THE INVENTION

This summary is provided to introduce a selection of concepts that are further described below in the Detailed Description. This summary is not intended to identify key or essential features of the claimed subject matter, nor is it to be used as an aid in limiting the scope of the claimed subject matter.

Aspects of the disclosure relate to a method for determining fluid properties. The method includes obtaining a density of a fluid and obtaining a Marsh funnel time associated with the fluid. The density of the fluid and the Marsh funnel time is provided to a processor. The processor derives properties of the fluid from the fluid density and the Marsh funnel time. A machine-learning algorithm is applied to the properties of the fluid. The machine-learning algorithm determines a plastic viscosity and a yield point of the fluid. Output of the machine-learning algorithm is stored for future use. Properties of the drilling fluid are adjusted based on the output of the machine learning algorithm.

Aspects of the disclosure relate to a system for determining fluid parameters. The system includes a Marsh funnel, a data-acquisition unit operatively coupled to the Marsh funnel, and a processor coupled to the data-acquisition unit. A memory is coupled to the processor. The processor is operatively coupled to a drilling fluid system.

Aspects of the disclosure relate to a method for monitoring fluid properties. In an embodiment, the method includes receiving, by a system, an input including a Marsh funnel time, calculating fluid properties based, at least in part, on a trained model of the system, and outputting the calculated fluid properties. In some embodiments, the trained model is a machine learning algorithm. In some embodiments, the method includes updating the trained model based, at least in part, on at least one of a past fluid measurement report and a present fluid measurement report. In some embodiments, the system can be, without limitation, a computer, an application, a graphical user interface of a program, a mobile application, a facility data gathering device, or combinations thereof.

In some embodiments, the input includes a set of dial readings. In some embodiments, the calculated fluid properties is a mud check output. In some embodiments, the calculated fluid properties are used to calibrate a real-time fluid monitoring system. In some embodiments, the input is a single value. In some embodiments, the calculated fluid properties are a synthetic set of dial readings. In some embodiments, the calculated fluid properties are at least one of a yield point and a plastic viscosity.

BRIEF DESCRIPTION OF THE DRAWINGS

A more complete understanding of the subject matter of the present disclosure may be obtained by reference to the following Detailed Description when taken in conjunction with the accompanying Drawings wherein.

DETAILED DESCRIPTION

Figure 1A:
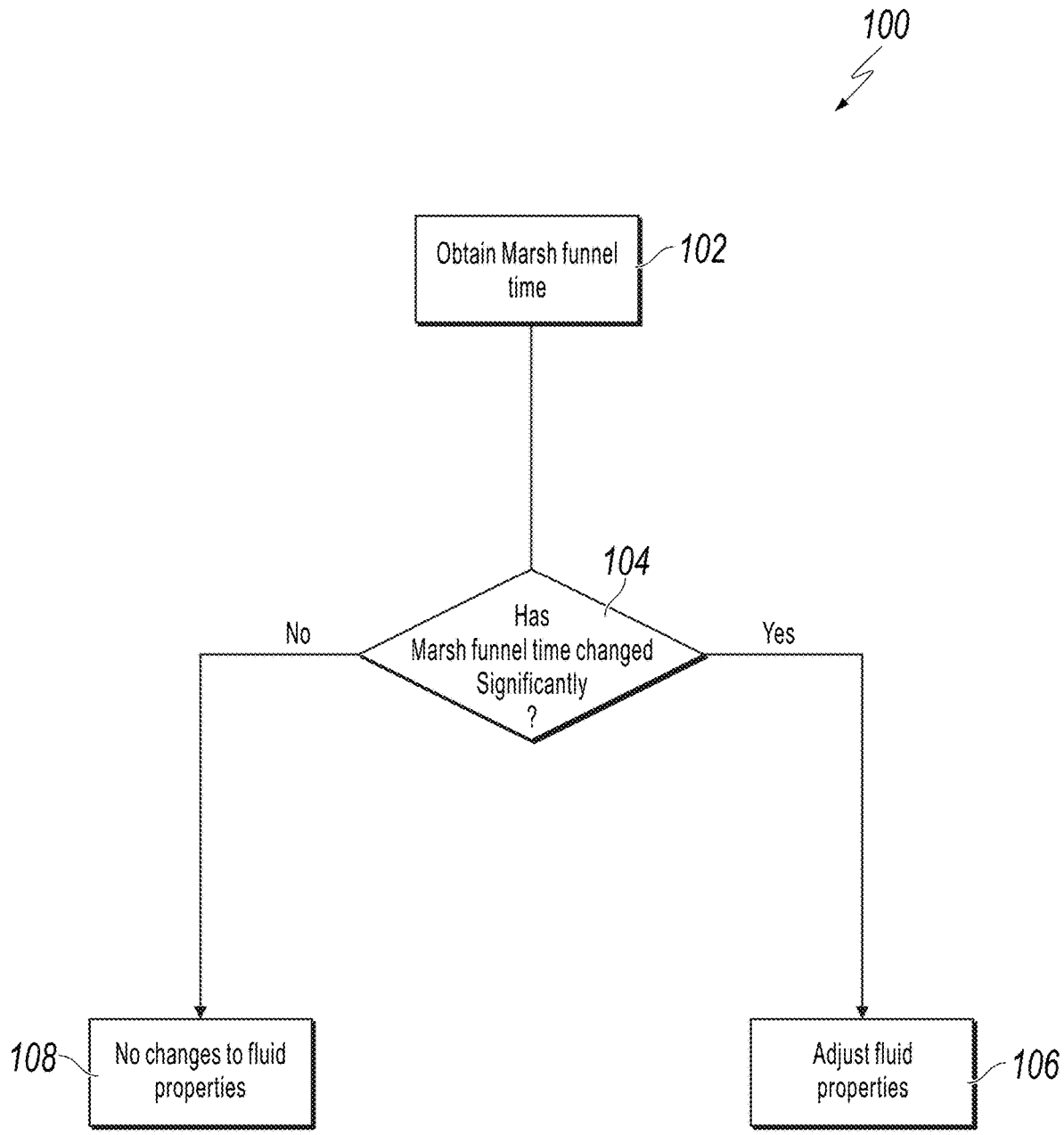
FIG. 1A is a flow diagram illustrating a current process for obtaining drilling fluid data from a Marsh funnel.

It is to be understood that the following disclosure provides many different embodiments, or examples, for implementing different features of various embodiments. Specific examples of components and arrangements are described below to simplify the disclosure. These are, of course, merely examples and are not intended to be limiting. The section headings used herein are for organizational purposes and are not to be construed as limiting the subject matter described.

A two-parameter model requiring only density and Marsh funnel time is disclosed herein to provide a detailed rheological analysis of fluids. An example below describes a simple but accurate method of transforming Marsh funnel times into viscosity measurements in conventional units that are equivalent to those obtained across the various shear rates recorded in oilfield mud reports.

Predicting PV and YP from Marsh Funnel Time

The Marsh funnel is a simple device and was the first oilfield instrument used for measuring and estimating fluid viscosity. Ease of operation and fast results are two reasons it has remained in use since being introduced by H. N. Marsh in 1931, despite other advances in rheometry. The Marsh funnel is included in the API recommended practices for the field-testing of water-based and oil-based drilling fluids.

A distinction has been made by some between rheometers and viscometers, with the former having the capability of providing measurements under different flow conditions whereas viscometers measure fluids under a single flow condition. Following this distinction, the Marsh funnel would be classified a viscometer while the conventional six-speed devices are rheometers. However, findings from the example presented herein demonstrate that this may not necessarily be the case with the Marsh funnel, owing to the range of shear experienced in the funnel.

A closer inspection of the funnel's flow characteristics reveals relationships between the flow rates, shear rates, wall shear stress, flow coefficient, and the Marsh funnel time that exist, but are not readily apparent. Applying the conical geometry of the Marsh funnel, the funnel time (i.e. the time it takes for 1 quart of a fluid to flow through the funnel) is used to calculate the shear rates and wall shear stress at the various heights across the funnel. Most drilling fluids yield shear rates that exceed the maximal 1022 $s^{-1}$ recommended in the API procedures. The rates of shear from the funnel are then interpolated to match those attained at the six standard rotational speeds used in the oil industry (i.e., 3, 6, 100, 200, 300, and 600 rpm). In this way, the Marsh funnel times together with the density are used to deduce the corresponding dial readings obtainable from a rotational rheometer at corresponding speeds.

The density of fluids is a parameter as it provides additional pressure for the flow. This is measured using a mud balance apparatus. Typically, the denser of two similarly viscous fluids will have a less funnel time. Together with the shear rates and fluid density, other relevant derivative aspects of the flow (viz., nominal height, flow coefficient, differential pressure and wall shear stress) are combined to build models for predicting the dial readings at corresponding shear rates. The statistical concepts of gradient descent, gradient boosting, and decision tree bootstrap aggregating are implemented on two ensemble machine learning algorithms: Random Forest and XGBoost. They build robust models which take only two raw readings (density and funnel time) to predict rheological readings at various shear rates, so that the plastic viscosity and yield point can be determined. A third method is also applied, employing polynomial regression.

Three variant versions of ensemble learning are discussed herein: Multivariate Random Forest, XGBoost and Polynomial Regression. Mud test results from 263 drilling muds used to drill West Texas wells were applied to populate and train the models.

Decision trees by themselves alone are generally weak learners, are susceptible to high variance and tend to lack a high degrees of accuracy on predictions. An all-purpose approach such as bootstrap aggregation aims to reduce the variance when applied to decision trees. Ensemble learning methods work by taking multiple algorithms or the same algorithm multiple times to arrive at a result better than the original.

Random Forest is a bootstrap aggregating (bagging) method developed by Leo Breiman (2001) which combines classifications of training sets generated randomly. A random subset of data points is chosen from a training set and used to build a decision tree associated with these selected data points. The number of trees to be built is then chosen and the process is repeated numerous times over again, yielding numerous regression decision trees independent of each other. Each of the trees is used to predict and assign a value for a new data point by averaging the predictions from all trees. In this manner, variance is reduced and overfitting is limited.

FIG. 1A is a flow diagram illustrating a current process 100 for obtaining drilling fluid data from a Marsh funnel. At block 102, a Marsh funnel time is obtained. At block 104, it is determined if the obtained Marsh funnel time has changed significantly. If, at block 104, it is determined that the Marsh funnel time has changed significantly, the process 100 proceeds to block 106 where further testing is undertaken to better determine the cause of the change in Marsh funnel time and the meaning behind the change in Marsh funnel time. If, at block 104, it is determined that the Marsh funnel time has not changed significantly, then the process 100 proceeds to block 108, where no changes are made to the drilling-fluid properties.

Figure 1B:
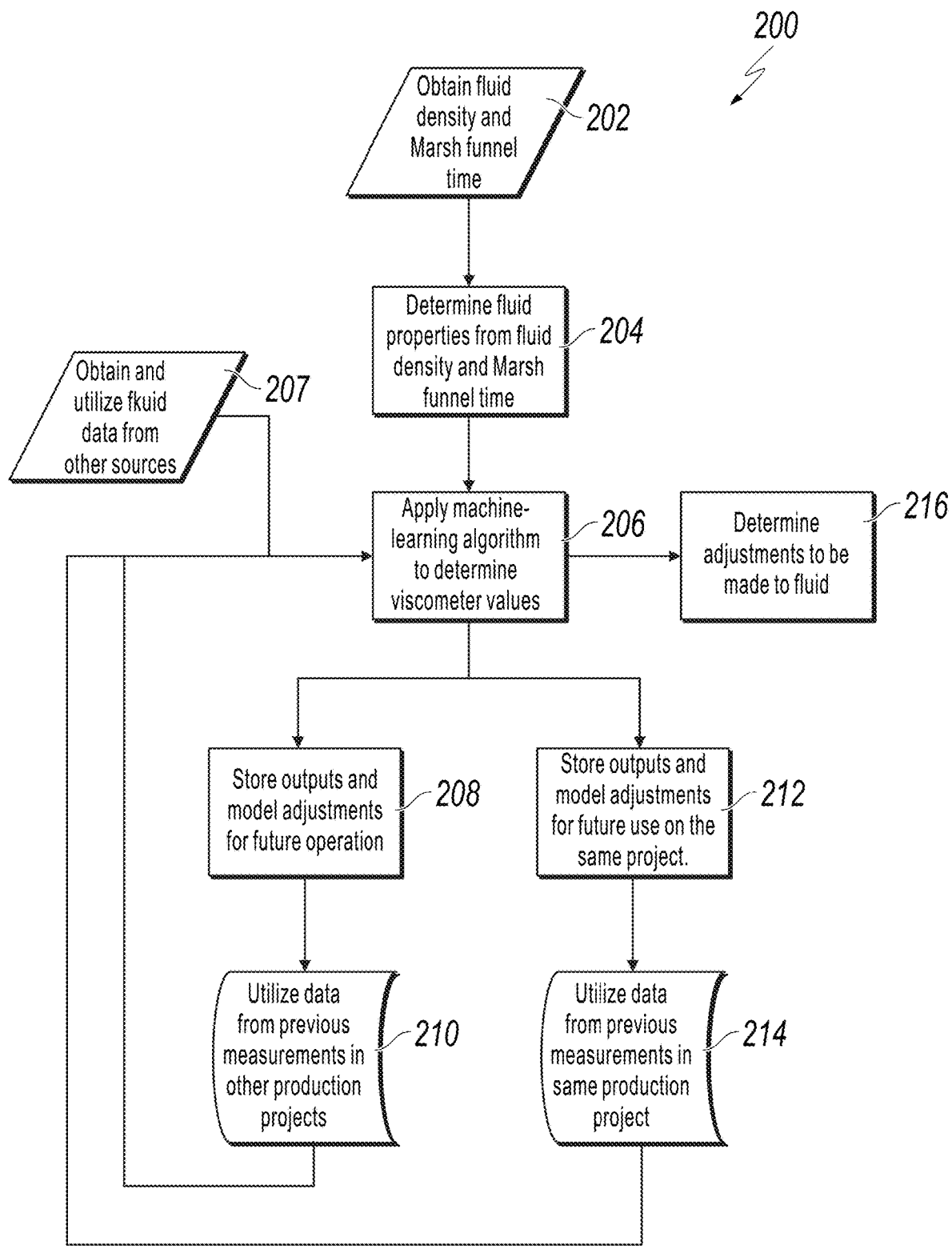
FIG. 1B is a flow diagram illustrating a process for obtaining drilling fluid data from a Marsh funnel according to aspects of the disclosure.

FIG. 1B is a flow diagram illustrating a process 200 for obtaining drilling fluid data from a Marsh funnel. At block 202, drilling fluid data is obtained from a Marsh funnel. In various embodiments, the drilling fluid data includes, for example, the density of the fluid and the Marsh funnel time. In various embodiments, the drilling fluid data may be obtained manually; however, in other embodiments the collection of data from the Marsh funnel may be automated. In such embodiments, the Marsh funnel may be operatively coupled to a processor and a data acquisition unit. At block 204, drilling fluid properties including, for example, shear effects, hydrostatic head effects, and geometry, and fluid shear stress versus shear rate relationships are derived from the Marsh funnel for the drilling fluid and the drilling fluid density. In various embodiments, the drilling-fluid properties are determined by a process or that is operatively coupled to the data acquisition unit. At block 206, a machine-learning algorithm is applied to the drilling-fluid properties. In various embodiments, the machine-learning algorithm expands and refines the drilling fluid properties and generates viscometer readings at, for example, 600 rpm, 300 rpm, 200 rpm, 100 rpm, 6 rpm, and 3 rpm; however, in other embodiments, the viscometer readings could be at any rpm reading. In various embodiments, the machine-learning algorithm determines a plastic viscosity (PV) and a yield point (YP) of the drilling fluid. The machine-learning algorithm applies fluid data obtained from other drilling sources and acquired at block 207. In various embodiments, fluid data obtained from other sources could come from, for example, previous tests in the same well or facility using a Marsh funnel or other fluid-property tests such as, for example, Coriolis meters, other rheometer or viscometer instruments. In various embodiments, the fluid data from other sources could be input manually or automatically into the data acquisition unit. At block 208, output data from the machine learning algorithm including, for example, model adjustments and drilling-fluid data are stored for use in future operations. At block 210, the information from block 208 is aggregated and utilized by the machine-learning algorithm for future analysis on other plants, wells, rigs, completion, production, or operation facilities.

Still referring to FIG. 1B, at block 212, output data from the machine learning algorithm including, for example, model adjustments and drilling-fluid data are stored for future use in the current operation. At block 214, data from block 212 including for example, data from previous measurements is aggregated and utilized by the machine-learning algorithm for future analysis on the same plant, well, rigs, completion, production, or operation facility. At block 216, the machine-learning algorithm outputs a plastic viscosity (PV) and a yield point (YP) of the drilling fluid. In various embodiments, the output of the machine-learning algorithm facilitates decisions concerning adjustment of fluid properties and operating parameters. In various embodiments the drilling-fluid adjustments can be manual or may be automated. In such embodiments, the processor on which the machine-learning algorithm is present is operatively coupled to an addition section of a mud system such that addition of additives to the drilling fluid can be controlled in an effort to regulate the properties of the drilling fluid on an automated basis. In various embodiments, drilling-fluid decisions could be a real-time or a near-real-time plot of the output of the machine-learning algorithm. As used herein, the term "near real time" means an instance of time that may include a delay typically resulting from processing, calculation and/or transmission times inherent in processing systems or web-based transmissions.

Figure 1D:
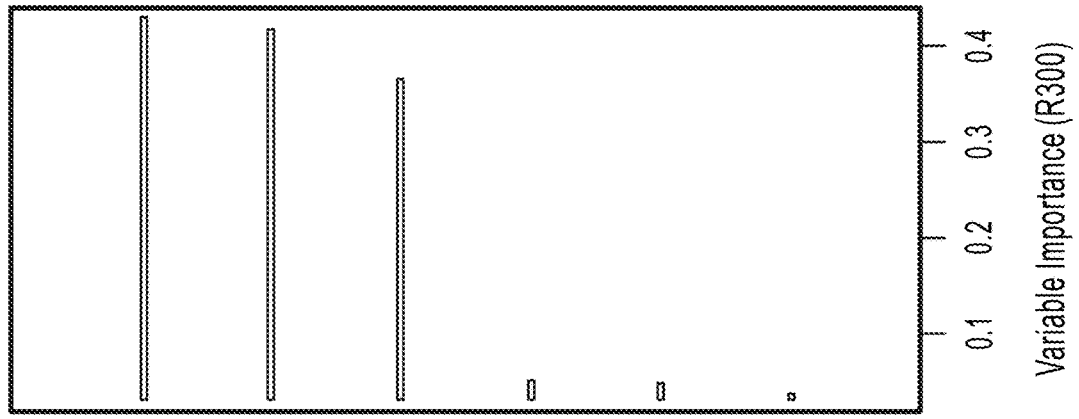
FIG. 1D is a plot illustrating variable importance of variables for a 300 rpm prediction model.
Figure 1C:
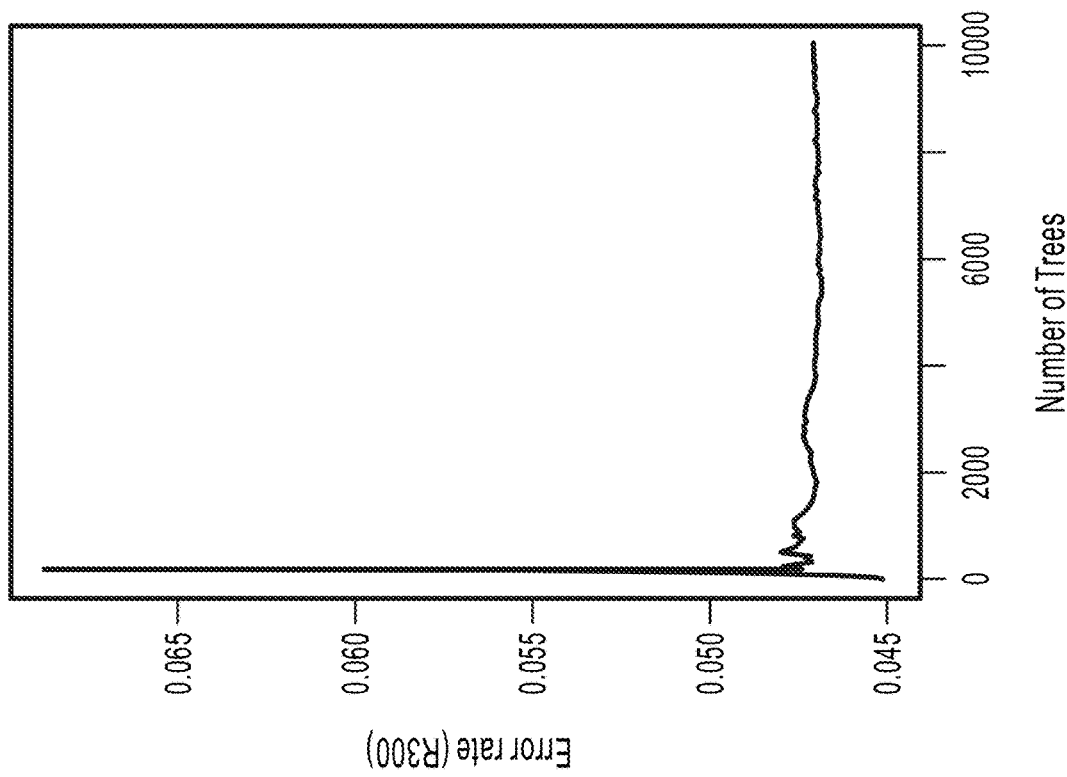
FIG. 1C is a plot illustrating decreasing out-of-bag error rate achieved by an ensemble of trees.
Figure 2:
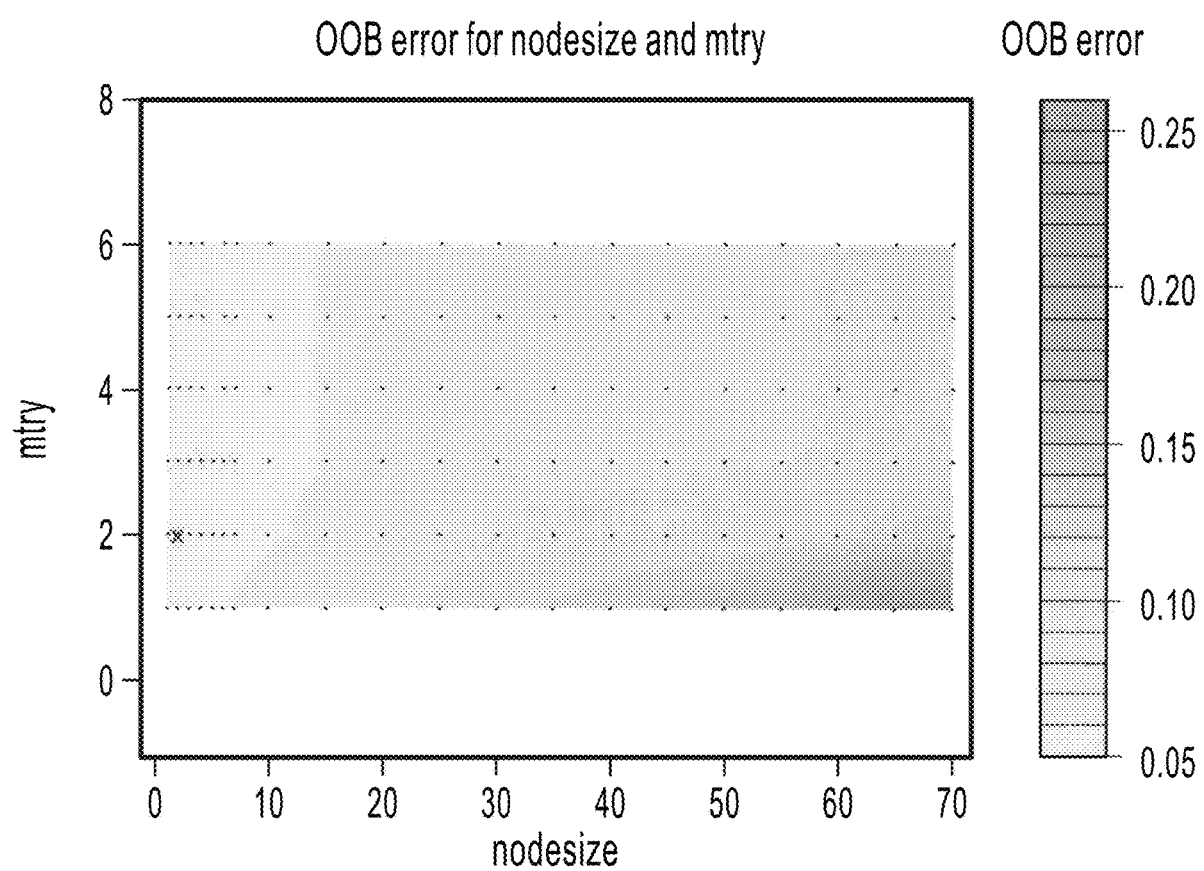
FIG. 2 is a contour plot showing the result of parameter tuning with out-of-box error.

FIGS. 1C-1D illustrate the gains achieved by aggregating many decision trees by use of random forests and boosting for the randomForestRSC model and the importance ranking of the variables. FIG. 2 is a contour plot of the results of tuning the 300 rpm model's hyperparameters: mtry and nodesize, using a grid search to select the combination with the least out-of-bag (OOB) error rate. Flow coefficient, funnel time and nominal height are by far the most important variables. In this case, the optimal mtry=2 and nodesize=2; where mtry is the number of variables randomly sampled as candidates for splitting a node, and nodesize is the Random Forest average number of unique cases in a terminal node. Additional analyses were made with the programming language, R, packages: rpart and party which are based on recursive partitioning using decision trees, but their accuracies did not surpass those of the models discussed in further detail in this study. By way of example, aspects of the disclosure are described herein as using the statistics/data analytics programming language "R"; however, in other embodiments, other programming languages such as, for example Python could also be utilized.

Separate models using univariate random forests (RF) and multivariate random forests (MRF) are built in this study for the 300 rpm and 600 rpm predictions. The forests were comprised of 5,000 trees and an attempt to show the importance of each of the parameters discussed in the previous section is made by considering the univariate case. The measure_importance function found within the randomForestExplainer package for the univariate RF has been used to display the importance of each variable as shown in Table 1. By considering the percentage increase in mean squared error (MSE), the increase in node purity and number of times each feature is picked as a root, it is observed that the flow coefficient, funnel time and nominal height are seen to be the most important parameters among the 5,000 trees in the forest. A variant of the random forest family, Multivariate Random Forest has been employed in this work to take full advantage of its unique implementation of the Mahalanobis distance as a measure of node cost (rather than the less accurate Euclidean distance) thereby capturing the distance between sample points and mean of the node along the principal component axes. The random forest approach is known to be powerful and accurate and gives good performance on both linear and non-linear problems.

TABLE 1

Measure of Importance of Random Forest Variables

| Parameter | % Increase MSE | Increase Node Purity | No. of Trees | Mean Minimum Depth | No. of Nodes | Times a Root |
|---|---|---|---|---|---|---|
| Flow Coefficient (gal per min.) | 0.47191403 | 76.989202 | 5000 | 1.24 | 72734 | 1493 |
| Pressure Differential (psi) | 0.04580562 | 13.868096 | 5000 | 1.9078 | 72098 | 527 |
| Density (lb/gal) | 0.03001831 | 3.638333 | 5000 | 2.462 | 47175 | 19 |
| Funnel Time (sec) | 0.39171182 | 64.964844 | 5000 | 1.5488 | 51535 | 1274 |
| Height | 0.39187602 | 64.694699 | 5000 | 1.5606 | 49902 | 1281 |
| Wall Shear (Pa) | 0.04290151 | 9.717795 | 5000 | 2.2383 | 68931 | 406 |

Figure 3:
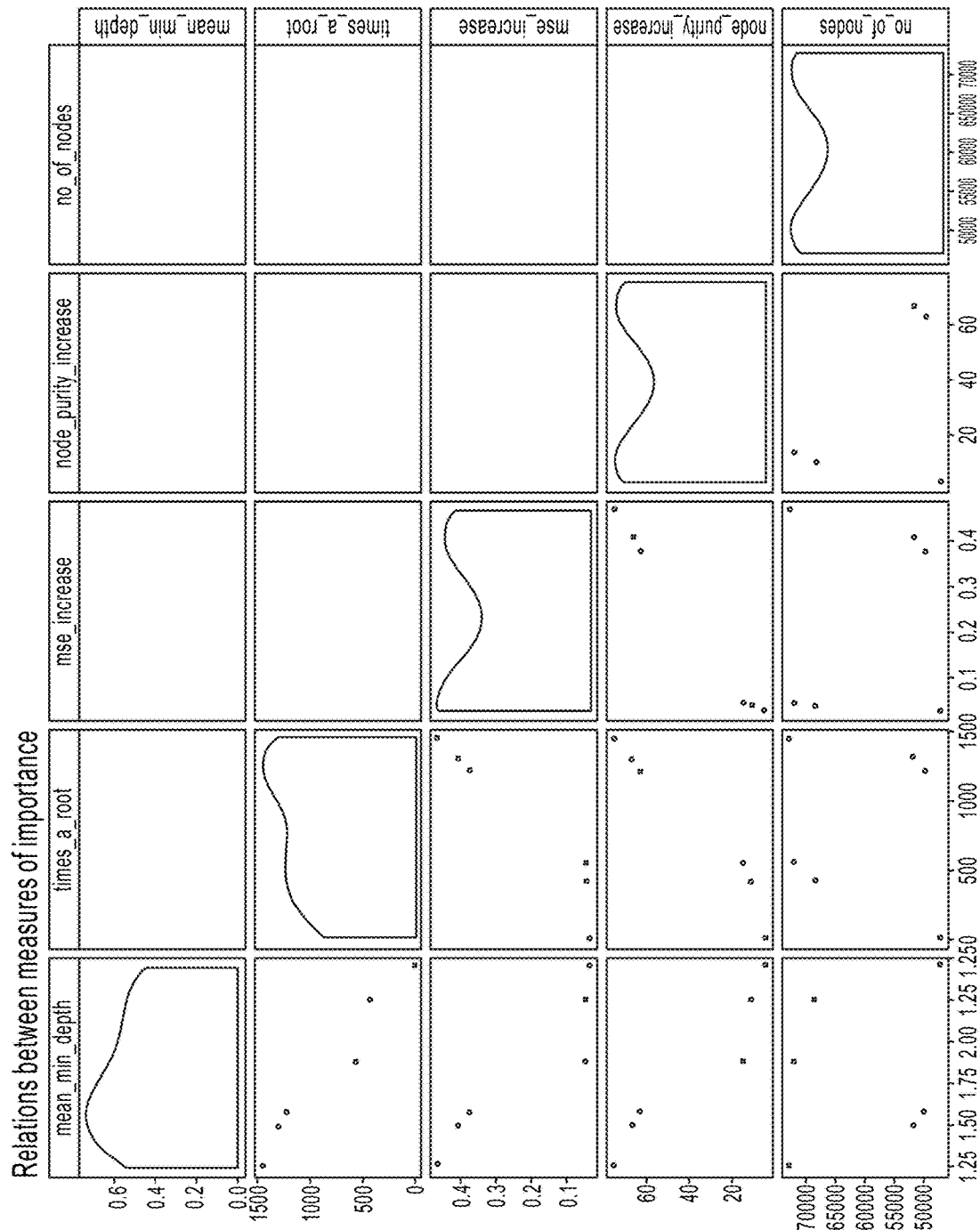
FIG. 3 is a matrix comparing importance of variable pairs. The row labels serve as the y-axis for the graphs on the same row, while the column labels serve as the x-axis for the graphs on the columns.

The correlations between the various measures of importance for the 300 rpm RF model are presented with a matrix scatter plot (FIG. 3). The percentage mean square error (MSE) increase, node purity increase and number of times picked as a root exhibit the best correlations. As with the randomForestSRC algorithm, the three parameters identified as most important, —flow coefficient, funnel time and height—accordingly all score high on the top three measures of importance.

Gradient Boosting XGBoost

Turning to the boosting approach, predictions from decision trees are improved by growing trees sequentially using knowledge derived from those grown previously. Contrary to bagging, bootstrap sampling is not applied here; rather trees are fitted on improved versions of the initial data set. XGBoost is a gradient boosting algorithm which typically utilizes three elements: a squared error (as a type of loss function to be optimized), a decision tree (as the weak learner with low bias and high variance, for making predictions) and an additive model for adding trees to minimize the squared error. Gradient descent is used to minimize the loss function when adding weak learners. Parameters such as coefficients in a regression equation are minimized with a functional gradient descent approach. Trees are added individually while retaining the existing trees and following the gradient towards a minimized squared error.

Figure 4:
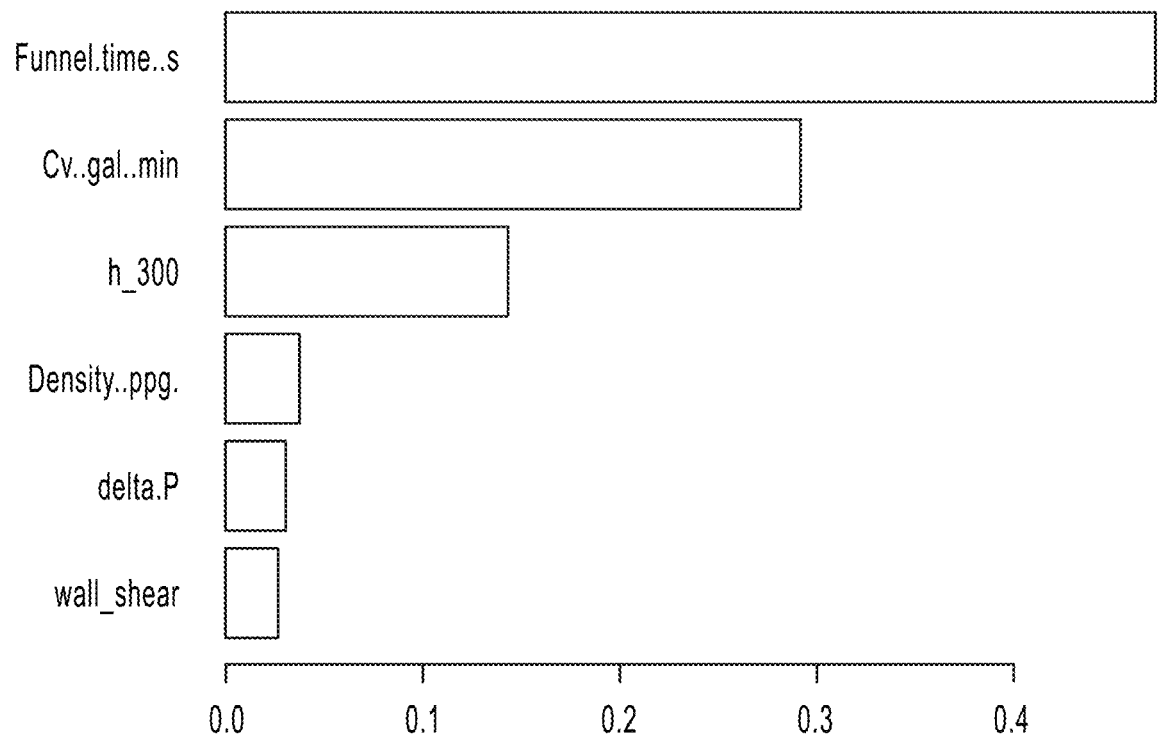
FIG. 4 is a plot illustrating importance of each parameter across all predictions for the 600 rpm XGBoost model.

FIG. 4 is the variable importance graph across all predictions for the 600 rpm XGBoost model. It indicates that the funnel time, flow coefficient, and nominal height are the most important variables across all predictions. It is important to note that this is not an absolute conclusion and would vary depending on the values of hyper-parameters selected. In this case we have chosen (eta=0.0005, max_depth=4, subsample=0.25, colsample_bytree=0.5, nround=9474 and set.seed=1) to arrive at this importance ranking. Cross validation was done on the training data set to help determine the best settings for the parameters.

Figure 5:
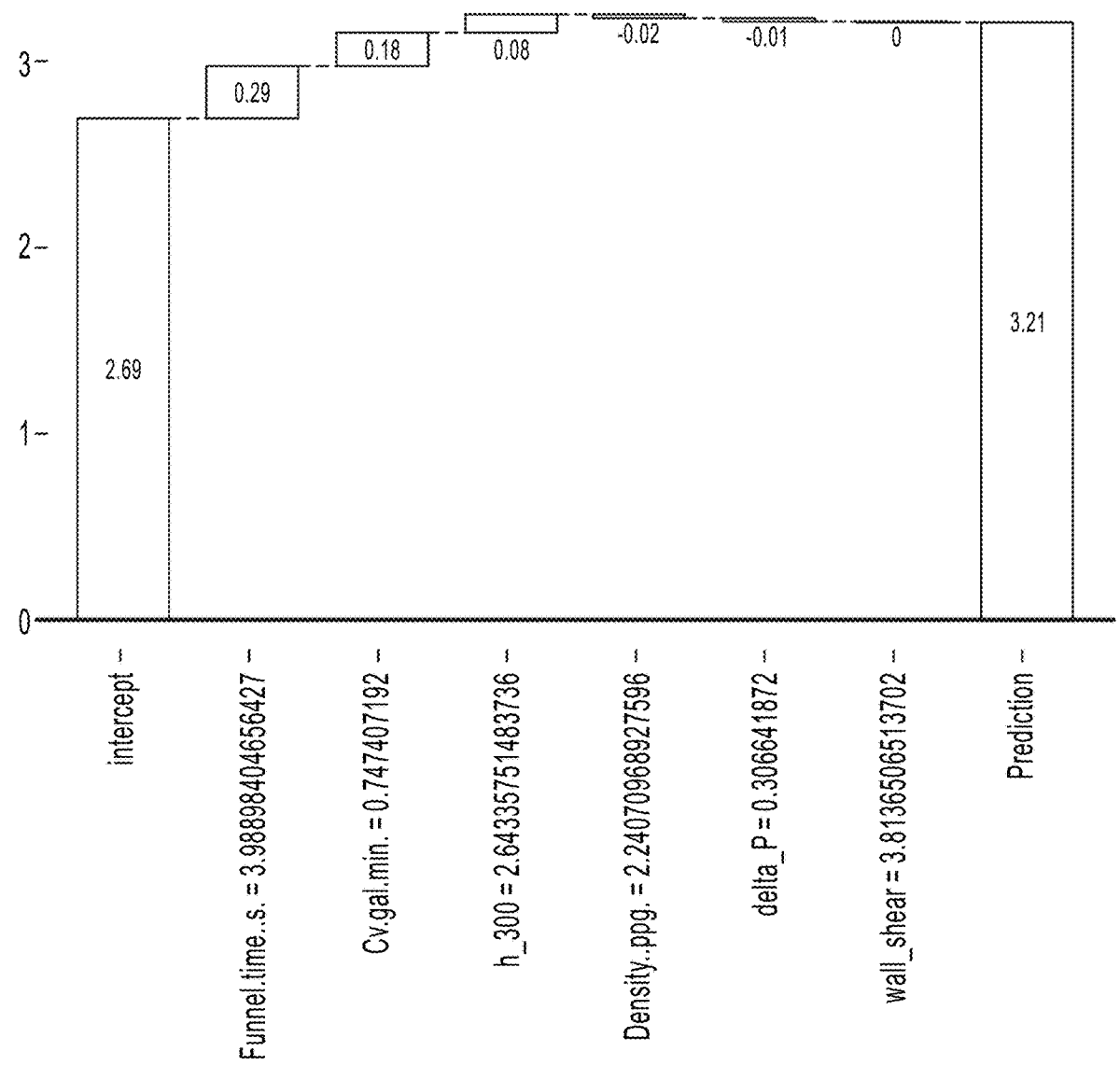
FIG. 5 is an explanation of the effect of each variable on an absolute prediction.

Next, we delve in deeper with the XGBoost Model Explainer (xgboostExplainer) package in the statistical software, R, and select an individual row in the training set to analyze its performance and understand how every prediction is made. This algorithm uses the log-odds prediction and breakdown the impact of each feature by weight. For a regression type problem as we have, the prediction equals the overall weight of the log-odds. FIG. 5 shows the effect of each variable on the absolute prediction of 3.21 from this particular row of data, which is the fourth mud sample in the test set as described in the discussion section of this paper.

The density, differential pressure and wall shear all pull down the value of the prediction, but only slightly since these parameters carry the least weight in the model. Noteworthy is the fact that the flow coefficient term incorporates the fluid density, which is the second most important feature in the model and one of the only two inputs. The only other raw input to the model is the funnel time, which not surprisingly is of utmost importance to the model's prediction of viscosity in the forms of 300 RPM and 600 RPM dial readings.

Figure 6:
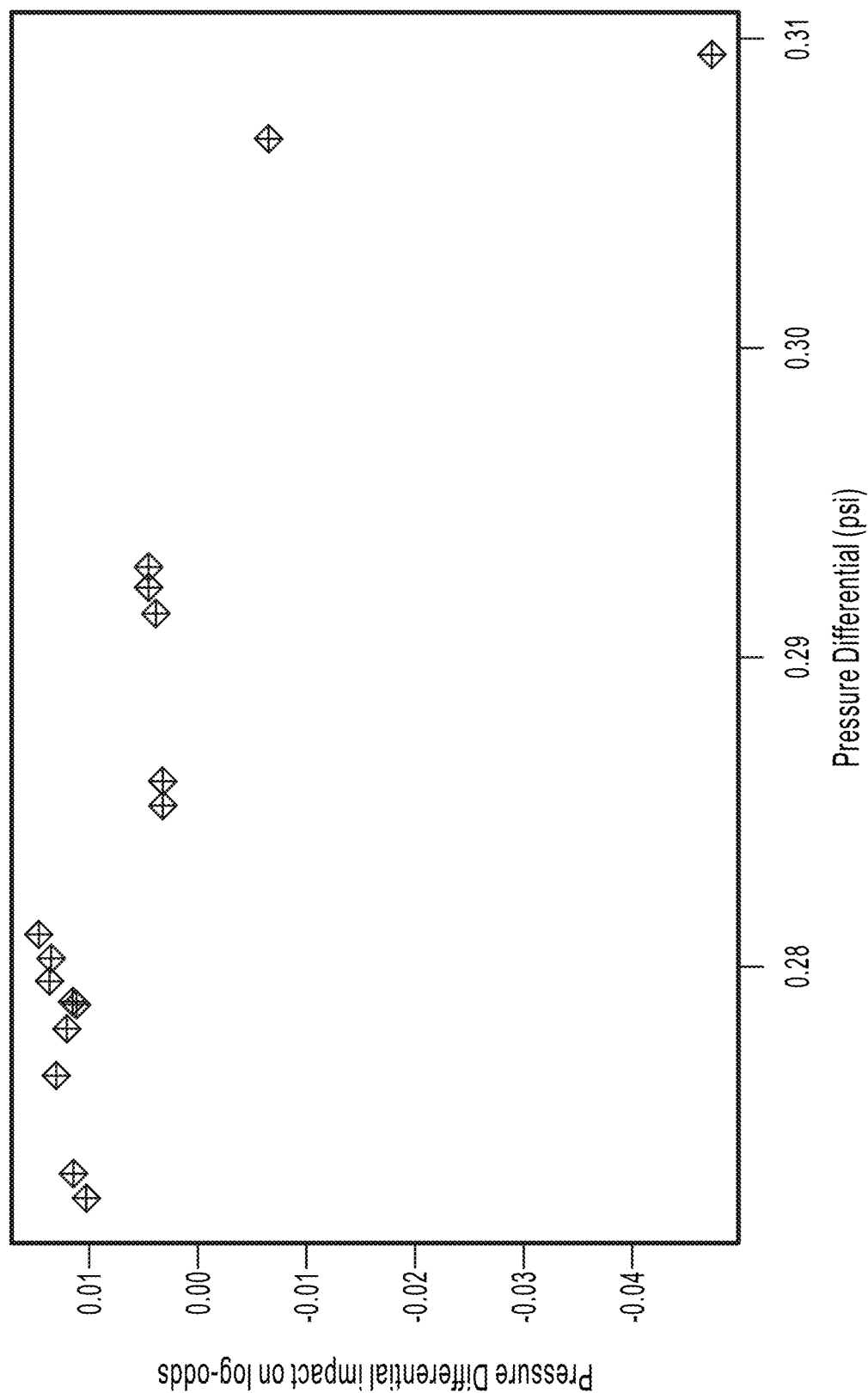
FIG. 6 illustrates the impact of flow coefficient on log-odds against the flow coefficient.

In FIG. 6 the impact of the pressure differential on log-odds against the values of the pressure differential (psi) is portrayed, showing that the parameter had little significance and did not contribute much to the decision making in the model. The impacts of features depend on the specific paths taken by the observation through the ensemble of trees, i.e. how frequently they were involved in making important decisions by the model. Each point is one mud sample from the test set. The pressure differential of the mud is plotted on the x-axis; the impact of the pressure differential on the log-odds of the predicted 300 rpm is plotted on the y-axis. The non-linearity in the data is adequately represented by the xgboostExplainer without being limited by straight lines as with logistic regression or steps as with decision trees or random forests.

Multivariate Polynomial Regression

Unlike the previous two models discussed above, modelling with polynomial regression offers advantages with respect to the explicability of terms, as well as being able to obtain representative equations from the model. Below are equations for both the 300 rpm and 600 rpm polynomial models for predicting rheometer dial reading from Marsh funnel experiments.

The 300 rpm model was more accurate, with an adjusted R-squared value of 0.9411, whereas the 600 rpm model had an adjusted R-squared of 0.93. Both were huge increases from an attempt to calculate the nominal height by linear interpolation. This highlights the importance of calculating the nominal height correctly by use of cubical interpolation to capture the non-linearity in the rate of change of height with time in the cone.

The results from the Marsh funnel tests conducted on 24 new drilling muds used to drill real wells in West Texas are discussed herein. The univariate random forest (RF), multivariate random forest (MRF), and the XGBoost gradient boosting technique were used for building models both for the 300 rpm and 600 rpm predictions. A literature survey suggested that boosted trees usually outperform bootstrap aggregated (bagged) trees and random forests. However, the MRF algorithm involved use of the Mahalanobis distance as a measure of node cost, hence capturing the correlations in the data by use of the off-diagonal covariance of the matrices, unlike most other random forests methods (e.g. randomForest, randomForestSRC) that are based on the Euclidean distance.

Figure 7:
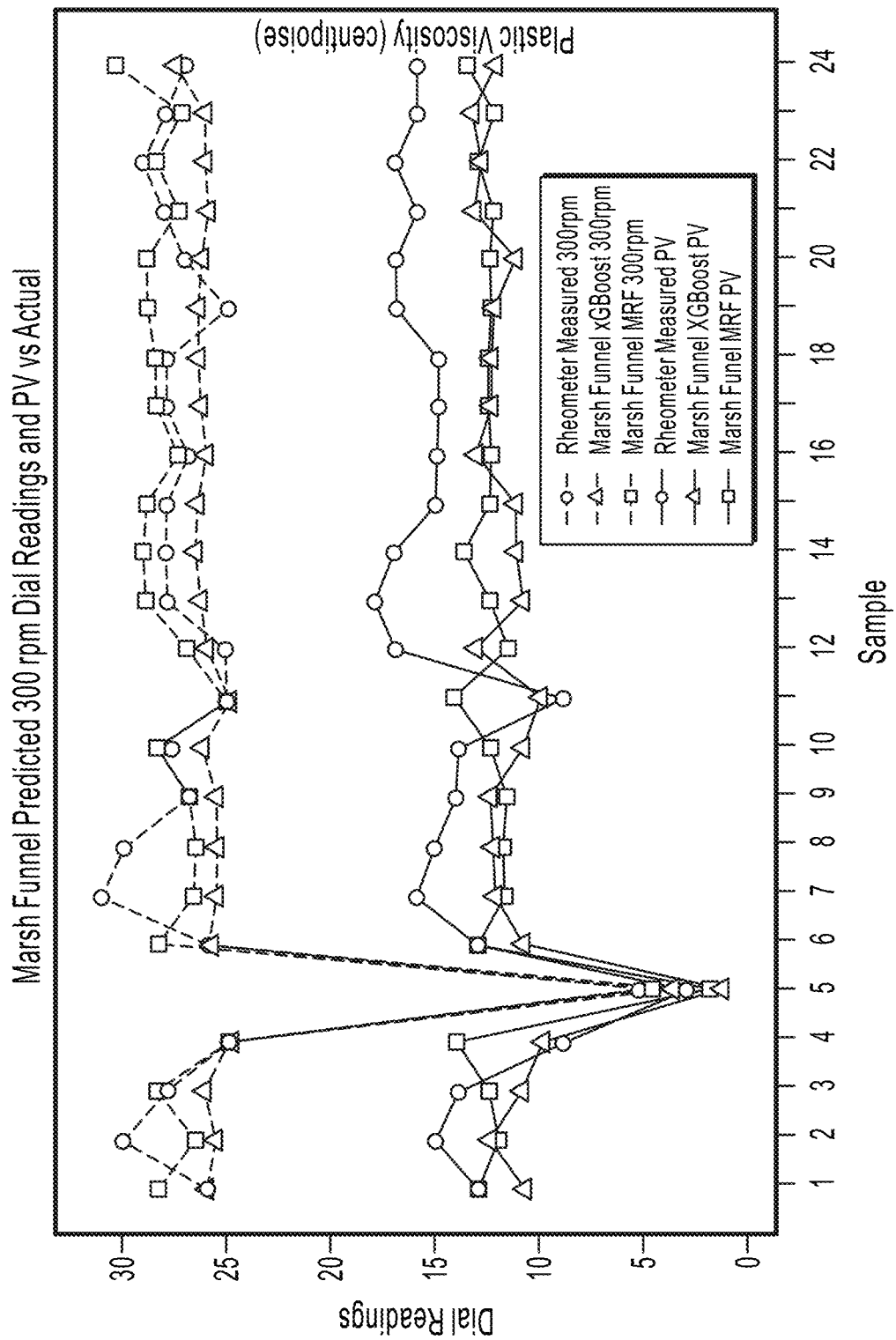
FIG. 7 illustrates predicted 300 rpm readings and plastic viscosity (PV) values from Marsh funnel tests compared with actual results from a conventional rheometer.
Figure 8:
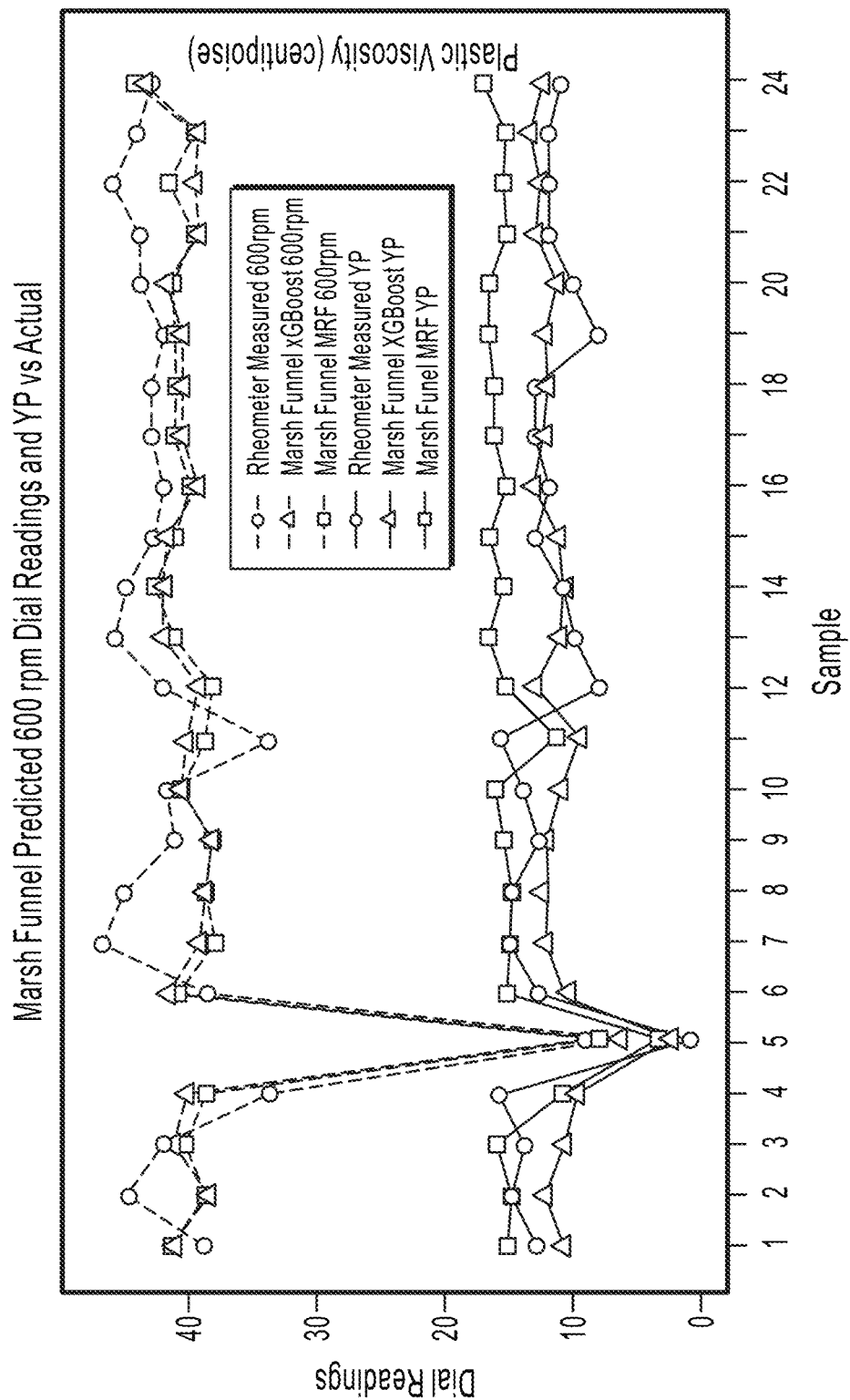
FIG. 8 illustrates predicted 600 rpm readings and yield point (YP) values from Marsh funnel tests compared with actual results from a conventional rheometer.

Other approaches such as the Gaussian process using R's mlegp package were applied with less accuracy. It was worth comparing the improved performance offered by MRF with results attained from XGBoost. FIG. 7 and FIG. 8 show how closely the predictions from the Marsh funnel tests using the MRF and XGBoost models (for the 300 rpm and 600 rpm readings) match actual results from a conventional rotational rheometer.

Figure 9A:
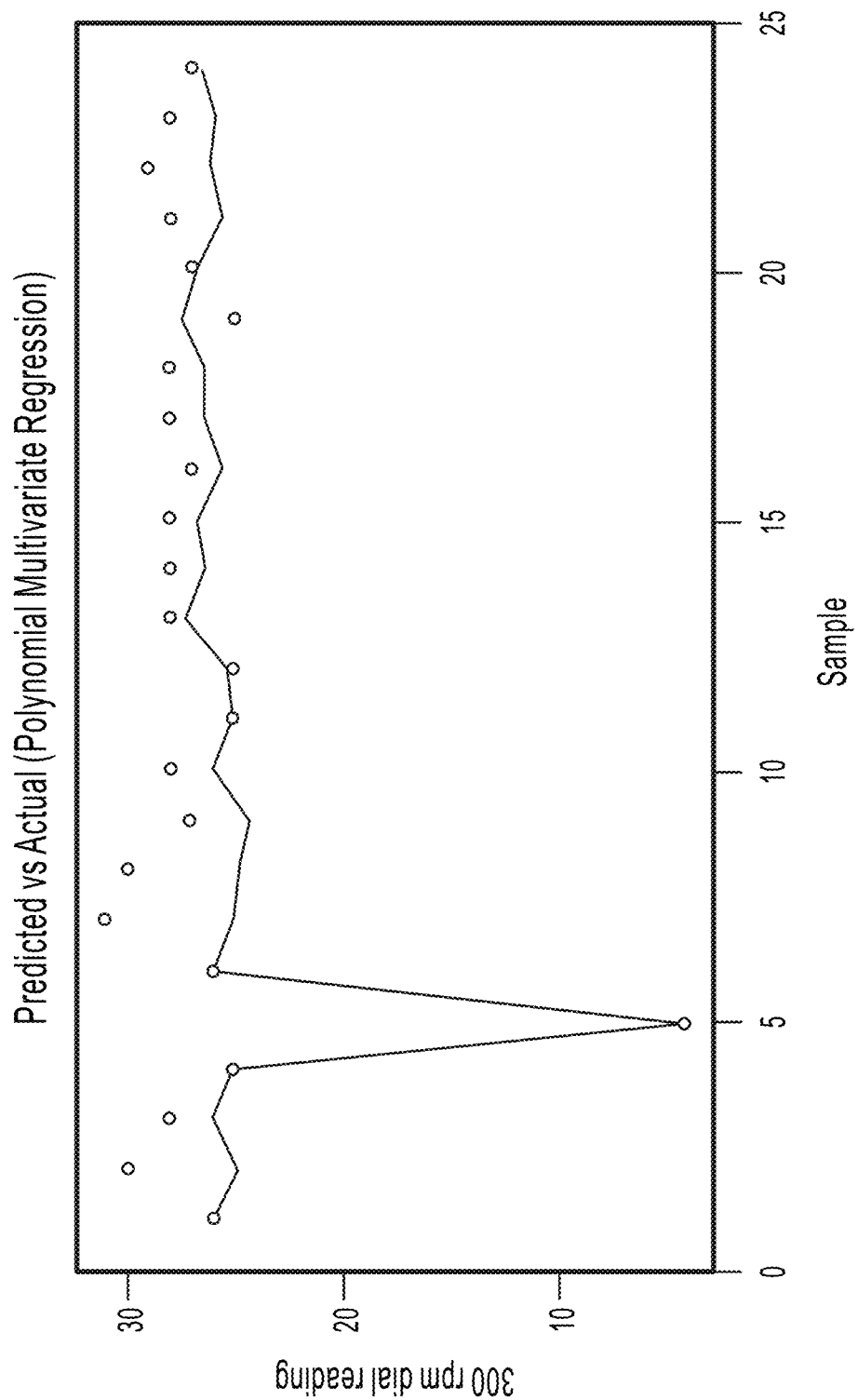
FIG. 9A illustrates polynomial regression model for 300 rpm readings. Red points are the actual values from mud tests on a conventional rheometer, while the blue line is the Marsh funnel prediction.
Figure 9B:
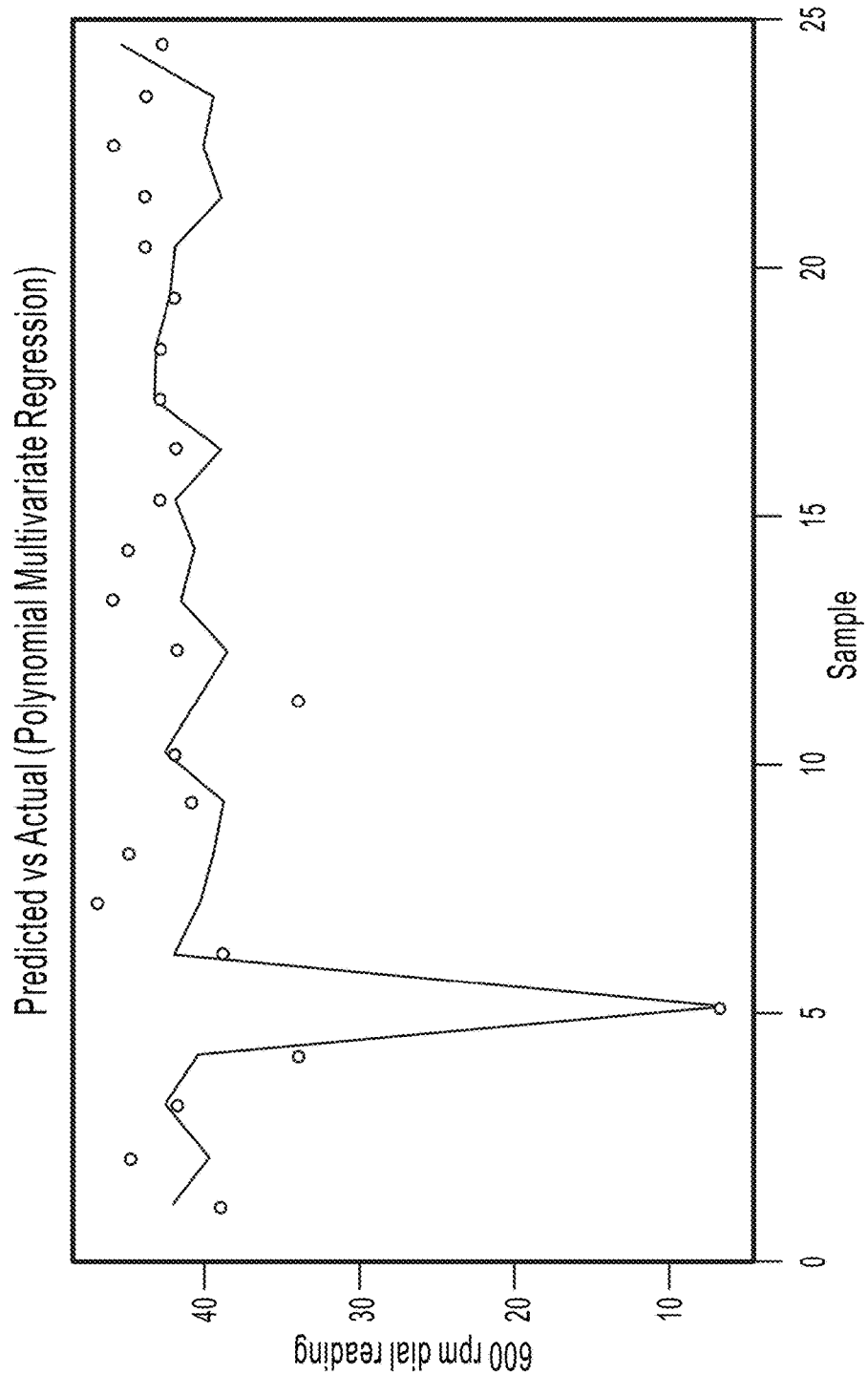
FIG. 9B illustrates polynomial regression model for 600 rpm readings. Red points are the actual values from mud tests on a conventional rheometer, while the blue line is the Marsh funnel prediction
Figure 10A:
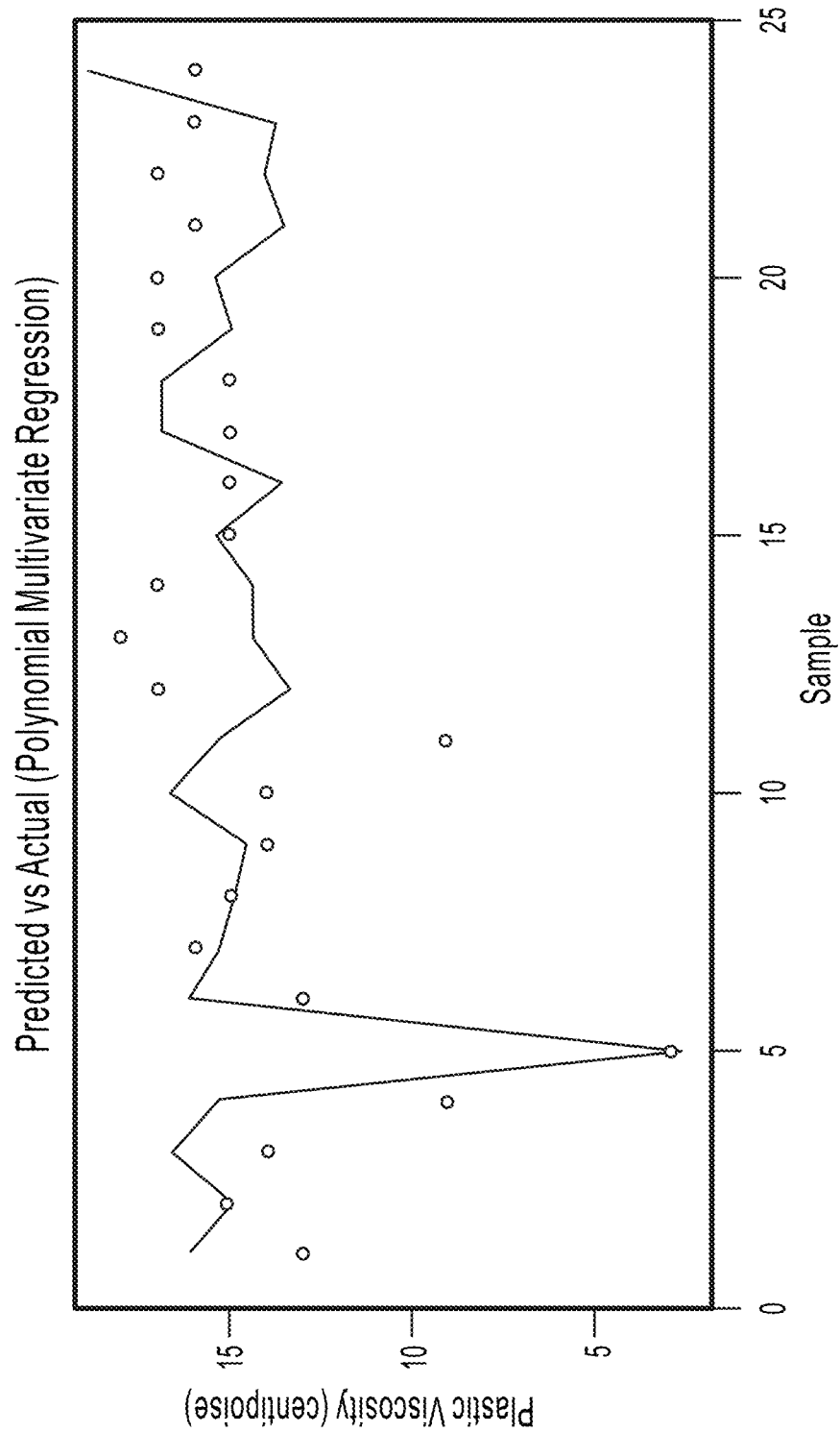
FIG. 10A illustrates polynomial regression model for plastic viscosity (PV) readings. Red points are the actual values from mud tests on a conventional rheometer, while the blue line is the Marsh funnel prediction.
Figure 10B:
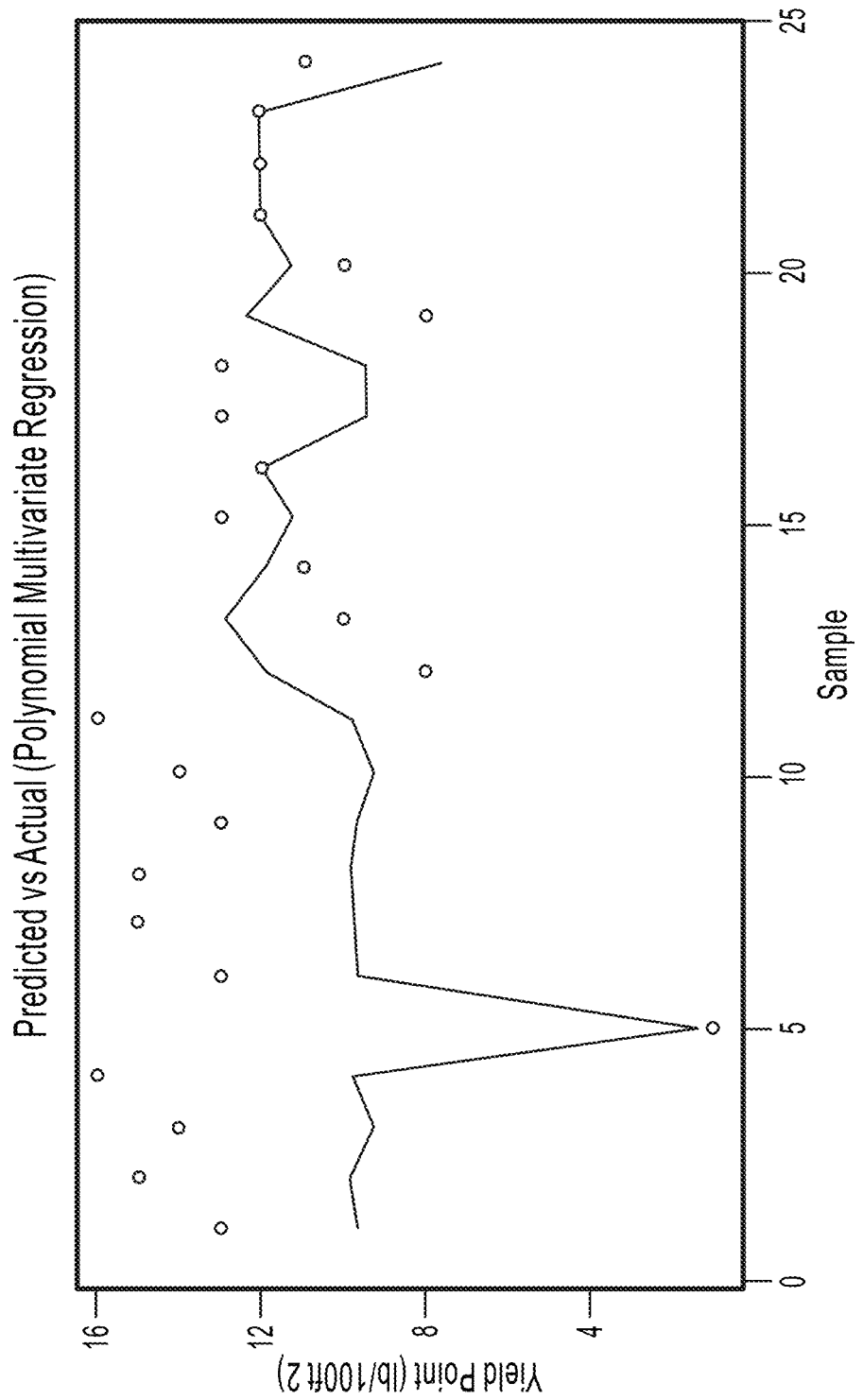
FIG. 10B illustrates polynomial regression model for yield point (YP) readings. Red points are the actual values from mud tests on a conventional rheometer, while the blue line is the Marsh funnel prediction.

For even more interpretability, it was desirable to apply multivariate polynomial regression to derive an equation for the model. FIGS. 9A-9B show the performance of the polynomial regression model in estimating the 300 rpm and 600 rpm, while FIGS. 10A-10B compare the results of the predicted plastic viscosity (PV) and yield point (YP) with actual values obtained from a conventional rheometer.

Figure 11:
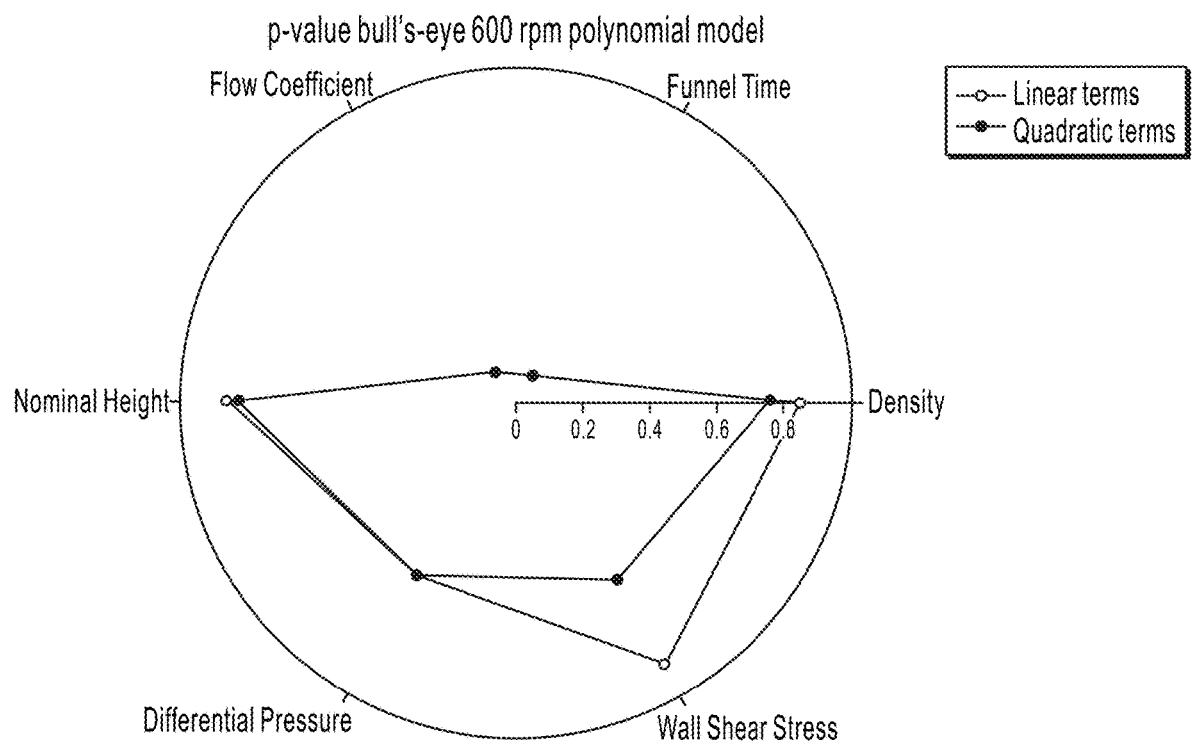
FIG. 11 illustrates radar charts of p-values (terms closer to center are more statistically significant) and pie charts of percentage variance explained.

FIG. 11 depicts the importance of each model predictor by way of the p-value and percentage of variance explained by each feature. It should be noted that features with lower p-values bear greater statistical significance, and so can be found nearer to the center of the radar chart. By convention, a value of 5% (i.e. 0.05) is often used as a cut-off for statistical significance. Not surprisingly, the funnel time proves to be the most important feature across both models, explaining three-quarters of the variance in the model, while density follows at 17%. The 300 rpm model also performs slightly better than the 600 rpm model in terms of adjusted R-squared, with a value of 0.9411 as opposed to 0.93. It is worth mentioning that this was a drastic increase from the 0.7376 and 0.664 adjusted R-squared values obtained, respectively, while applying linear interpolation to determine the nominal height.

Table 2, shown below, summarizes the results from the three models. The XGBoost model performed better than the univariate RF model on the 600 rpm readings. The metrics of choice were the root mean square error (RMSE) and the mean absolute error (MAE). Table 2, shown below, compares the three models with the RMSE and MAE metrics, demonstrating that the MultivariateRandomForest is best in 300 RPM, XGBoost is best in plastic viscosity (PV) and yield point (YP), and Polynomial Regression is best in 600 RPM.

TABLE 2

| Model | Test | | Plastic Viscosity | Yield Point | Metric |
|---|---|---|---|---|---|
| | 300 RPM | 600 RPM | | | |
| MultivariateRandomForest | 1.95646843 | 3.915552 | 3.534010168 | 4.159621412 | RMSE |
| XGBoost | 2.14968149 | 3.990971 | 2.678304338 | 2.7678577 | RMSE |
| Polynomial Regression | 2.453260177 | 3.836987 | 2.831320791 | 3.653389251 | RMSE |
| MultivariateRandomForest | 1.42611752 | 3.337413 | 3.193191708 | 5.884076 | MAE |
| XGBoost | 1.63233362 | 3.344824 | 2.218181833 | 2.155698333 | MAE |
| Polynomial Regression | 1.802855667 | 3.176342 | 2.331181833 | 3.069474 | MAE |

This study demonstrates that the Marsh funnel has strong potential as a predictor of rheological properties and can serve as a substitute to the state-of-the-art rotational rheometers. Owing to the vast range of shear witnessed in the funnel during a Marsh funnel test, it is possible to use the simple device to replicate results from more conventional, sophisticated, and expensive rheometers. Models were built using only two parameters (Marsh funnel time and density) which closely approximated results from conventional rheometers. Data from Marsh funnel tests has greater value than is typically accorded. Given that only the plastic viscosity (PV) and yield point (YP) readings were recorded in the field data used for building the training models, it was only possible to work on the 300 rpm and 600 rpm prediction models. However, by following the same methodology used in this example, it should be possible to achieve similar results for the 3, 6, 100, and 200 rpm readings. This example was based on 263 mud tests used for building the models, and another 24 samples for testing the performance.

Applications and Advantages

The Marsh funnel methods, as disclosed herein, can also be utilized as a continual calibration to the systems as disclosed herein. The gel strength measurement process involves the fluid sitting still for a prescribed period of time, usually 10 seconds, 10 minutes, 30 minutes, or at times up to an hour or more. After sitting still, the piezo-devices are activated and a measurements taken. The fluid remains at rest until the next time step and another measurement is taken. As with the previous methods, the algorithm uses trained machine learning algorithms to output gel strengths.

In some embodiments, the present disclosure relates to method of using a Marsh funnel to obtain a full range of shear strength versus rate readings. Previously, the Marsh funnel was discounted as little more than a qualitative spot check of a fluid's viscosity that was prone to misinterpretation and error. However, the methods presented herein turn the same readings into valuable sources of information about a drilling fluid's properties. The Marsh funnel is typically thought of as having limited use, or even having negative value, to quantify fluid properties on a wellsite. The methods disclosed herein leverage the fact the Marsh funnel has a standard geometry and measurement procedure, and along with an understanding of the drilling fluid, is able to generate a synthetic set of dial readings. This is done through an algorithm that takes a historical data set of limited size and develops a model that then only needs a single value, the Marsh funnel reading, to generate the synthetic dial readings with what amounts to a 30 to 60 second long procedure.

In some embodiments, the Marsh funnel reading is input into a computer, software programs, or a facility data-gathering device, commonly called Electronic Data Recorder (EDR) in the drilling industry. The algorithm is trained on a data set initially, and continues to be trained going forward at each fluid measurement report, or mud check, is input into the system. The synthetic dial readings are calculated and outputs to a system or format of choice.

The most common approach to testing drilling fluids on-site include the use of a mud check where a rotational viscometer is used to measure the fluid properties about twice a day. The Marsh funnel is used at a higher frequency, perhaps every 30 minutes to every few hours. However, these are used qualitatively and currently these methods are considered of low value. Other technologies do exist, however these technologies do not combine an easy to install solution with a small footprint that truly allows for continuous real-time measurements as provided by the systems and methods disclosed herein. The systems and methods of the present disclosure provide for easy installation, calibration, and maintenance. Furthermore, the systems and methods disclosed herein do not interfere with the fluid flow itself and thus is completely non-intrusive. The systems and methods disclosed herein allow for remote monitoring in situations where this would be advantageous. This could include, for example, dangerous sites and/or facilities, multiple sites, or measurement points with limited personnel to monitor fluid properties. In addition, the systems and methods disclosed herein allows for data to be sent in real-time to various parties involved in the processes, for example, well drilling, who will then be able to make better decisions based on real-time fluid properties.

In various embodiments, the Marsh funnel technique can be applied to obtain "synthetic" dial readings across all shear rates/rotary speeds of interest (typically 3, 6, 100, 200, 300 and 600 RPM). A commercially-available numerical simulation software is applied to build a model using computational fluid dynamics. Results from the numerical analysis are corroborated by analytical calculations that are then used to develop a statistical framework for predicting dial readings under various shear rates (3-600 RPM). Experimental results from more than 1500 mud tests are utilized to build ten machine learning algorithms modelling the rheological properties of the fluids. Their performances are evaluated to determine the best models based on three metrics: R-squared values, root mean square error and mean absolute error.

Predictions are performed on new mud data and comparisons are made among the ten predictive models broadly categorized into generalized regression models, decision tree-based techniques and miscellaneous approaches. The models show high predictive accuracies on new drilling fluid samples with the performances generally improving with increasing shear rates. A mathematical analysis of the geometry of the Marsh funnel has been utilized to establish a methodology to quickly and accurately perform rheological studies on fluids. Results from experimental, analytical, numerical and statistical studies all closely agree with each other.

The outcome of this study can readily be employed at the wellsite to obtain much value from the routine hourly Marsh funnel readings. This can serve as a quick substitute to infrequent conventional rheometer outputs, which are typically obtained only one to four times per day at the field. The rheological results and other derivates such as plastic viscosity (PV) and yield point (YP) are immediately produced after each Marsh funnel test. Informed decisions such as updating hydraulics modelling to improve ROP and hole cleaning can be thus be achieved.

Figure 12:
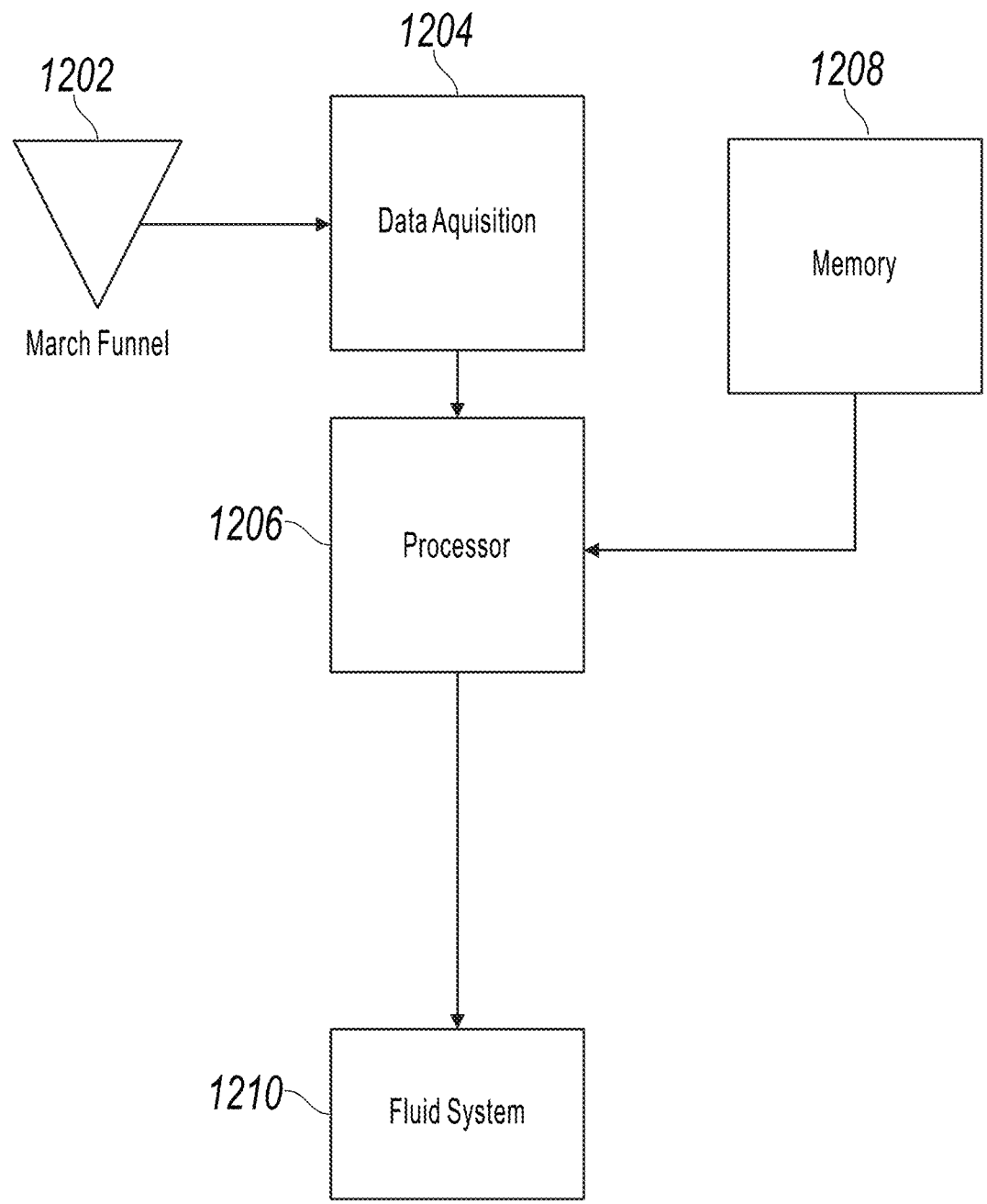
FIG. 12 is a diagrammatic illustration of a fluid-measurement system according to aspects of the disclosure.

FIG. 12 is a diagrammatic illustration of a fluid-measurement system 1200. The fluid-measurement system 1200 includes a Marsh funnel 1202. The Marsh funnel 1202 is operatively coupled to a data acquisition device 1204 such that measurements of fluid density and Marsh funnel time are automatically transmitted from the Marsh funnel 1202 to the data-acquisition device 1204. In various embodiments, the Marsh funnel 1202 could be filled by, for example, a gravity-actuated, pivoting, bucket. The bucket fills with fluid and, when the fluid level in the bucket reaches a predetermined level, gravity causes the bucket to tip and spill the fluid into the Marsh funnel 1202. Initially, the outlet of the Marsh funnel 1202 is plugged to prevent fluid exit. Upon removal of the plug, a timing device is started. The fluid exits the Marsh funnel 1202 into a volume-measurement device that measures one quart of fluid. In various embodiments, the volume-measurement device could be, for example, a one-quart container or an in-line volume measurement device. Once one quart of fluid has exited the Marsh funnel, the timing device is stopped and the time is communicated to the data-acquisition device 1204. A processor 1206 is coupled to the data-acquisition device 1204. A memory 1208 is coupled to the processor 1206. In various embodiments a machine-learning algorithm of a type described in any of the preceding paragraphs is present on the processor 1206. The processor 1206 is operatively coupled to a fluid system 1210 such that, responsive to an output of the machine-learning algorithm the properties of the drilling fluid may be altered automatically. In various embodiments, alteration of the drilling fluid may include a variety of actions and may include for example, increasing or decreasing a rate of addition of water to the drilling fluid. Alternatively, the drilling fluid may be altered by a chemical additive such as, for example, an addition of a gel or viscofying agent that is introduced to the drilling fluid. For example, responsive to a determination by the machine-learning algorithm, the processor may direct the fluid system to, for example, introduce a chemical additive, such as a gel or a viscofying agent, to the fluid for the purpose of adjusting one or more properties of the fluid.

Although various embodiments of the present disclosure have been illustrated in the accompanying Drawings and described in the foregoing Detailed Description, it will be understood that the present disclosure is not limited to the embodiments disclosed herein, but is capable of numerous rearrangements, modifications, and substitutions without departing from the spirit of the disclosure as set forth herein.

The term "substantially" is defined as largely but not necessarily wholly what is specified, as understood by a person of ordinary skill in the art. In any disclosed embodiment, the terms "substantially", "approximately", "generally", and "about" may be substituted with "within [a percentage] of" what is specified, where the percentage includes 0.1, 1, 5, and 10 percent.

The foregoing outlines features of several embodiments so that those skilled in the art may better understand the aspects of the disclosure. Those skilled in the art should appreciate that they may readily use the disclosure as a basis for designing or modifying other processes and structures for carrying out the same purposes and/or achieving the same advantages of the embodiments introduced herein. Those skilled in the art should also realize that such equivalent constructions do not depart from the spirit and scope of the disclosure, and that they may make various changes, substitutions, and alterations herein without departing from the spirit and scope of the disclosure. The scope of the invention should be determined only by the language of the claims that follow. The term "comprising" within the claims is intended to mean "including at least" such that the recited listing of elements in a claim are an open group. The terms "a", "an", and other singular terms are intended to include the plural forms thereof unless specifically excluded.

What is claimed is:

1. A method for determining at least one property of a fluid, the method comprising:
   obtaining a Marsh funnel time associated with the fluid;
   providing the Marsh funnel time to a processor coupled to a memory and a data acquisition unit;
   applying, via the processor, a machine-learning algorithm to the Marsh funnel time to determine the at least one property, wherein the at least one property comprises a synthetic set of dial readings for the fluid;
   storing output of the machine-learning algorithm for future use;
   adjusting, via the processor, the at least one property of the fluid based on the output of the machine learning algorithm.

2. The method of claim 1, wherein a density of the fluid and the Marsh funnel time is provided automatically to the processor via the data acquisition unit operatively coupled to the Marsh funnel.

3. The method of claim 1, wherein the output of the machine-learning algorithm is stored for future use in other production operations.

4. The method of claim 1, wherein the output of the machine-learning algorithm is stored for future use by a current production operation.

5. The method of claim 1, wherein the machine-learning algorithm utilizes fluid measurements from other sources.

6. The method of claim 1, wherein the adjusting comprises adding a gel or a viscofying agent to the fluid.

7. The method of claim 1, wherein the output of the machine-learning algorithm facilitates automatic adjustment of the at least on property of the fluid via the processor being operatively coupled to a fluid system.

8. A system for determining at least one fluid parameter of a fluid, the system comprising:
   a Marsh funnel configured to receive the fluid;
   a data-acquisition unit operatively coupled to the Marsh funnel and configured to collect a Marsh funnel time of the fluid;
   a processor comprising memory and coupled to the data-acquisition unit, the processor being configured to determine the at least one fluid parameter using a machine learning algorithm applied to the fluid Marsh funnel time, wherein the at least one fluid parameter comprises a synthetic set of dial readings for the fluid;
   wherein the processor is operatively coupled to a drilling fluid system to adjust the at least one fluid parameter based at least in part upon the synthetic set of dial readings.

9. The system of claim 8, wherein the Marsh funnel provides a density and a Marsh funnel time to the data acquisition unit.

10. The system of claim 8, wherein the machine-learning algorithm is present on the processor.

11. A method for monitoring at least one fluid property of a fluid, the method comprising:
  receiving, by a data acquisition system comprising a processor and a memory, an input comprising a Marsh funnel time associated with the fluid;
  calculating, by the processor, a synthetic set of dial readings based, at least in part, on a trained model of the data acquisition system using the Marsh funnel time; and
  adjusting, by the processor, in near real time the at least one fluid property of the fluid based at least in part upon the synthetic set of dial readings.

12. The method of claim 11, wherein the trained model is a machine learning algorithm.

13. The method of claim 11, comprising updating the trained model based, at least in part, on at least one of a past fluid measurement report and a present fluid measurement report.

14. The method of claim 11, wherein the data acquisition system comprises a computer, an application, a graphical user interface of a program, a mobile application, a facility data gathering device, or combinations thereof.

15. The method of claim 11, wherein the calculated at least one fluid property is a mud check output.

16. The method of claim 11, wherein the calculated at least one fluid property is used to calibrate a real-time fluid monitoring system.

17. The method of claim 11, wherein the input is a single value.

18. The method of claim 11, wherein the calculated at least one fluid property is at least one of a yield point and a plastic viscosity.

* * * * *